United States Patent
Kolins et al.

(10) Patent No.: US 9,138,500 B2
(45) Date of Patent: Sep. 22, 2015

(54) APPARATUS AND METHOD FOR SANITIZING STETHOSCOPE HEADS

(71) Applicant: William Beaumont Hospital, Royal Oak, MI (US)

(72) Inventors: Mark D. Kolins, Bloomfield, MI (US); Barry Siegel, Birmingham, MI (US)

( * ) Notice: Subject to any disclaimer, the term of this patent is extended or adjusted under 35 U.S.C. 154(b) by 0 days.

(21) Appl. No.: 14/357,523

(22) PCT Filed: Nov. 9, 2012

(86) PCT No.: PCT/US2012/064442
§ 371 (c)(1),
(2) Date: May 9, 2014

(87) PCT Pub. No.: WO2010/131253
PCT Pub. Date: Nov. 18, 2010

(65) Prior Publication Data
US 2014/0314622 A1    Oct. 23, 2014

Related U.S. Application Data

(60) Provisional application No. 61/557,619, filed on Nov. 9, 2011.

(51) Int. Cl.
| | |
|---|---|
| *A61L 2/18* | (2006.01) |
| *A61L 2/235* | (2006.01) |
| *A61B 7/02* | (2006.01) |
| *A61B 19/00* | (2006.01) |

(52) U.S. Cl.
CPC ... *A61L 2/18* (2013.01); *A61B 7/02* (2013.01); *A61B 19/34* (2013.01); *A61L 2/235* (2013.01)

(58) Field of Classification Search
CPC ........................................................ A61L 2/18
USPC .................................................. 422/28, 292
See application file for complete search history.

(56) References Cited

U.S. PATENT DOCUMENTS

| | | |
|---|---|---|
| 2005/0214185 A1 | 9/2005 | Castaneda |
| 2009/0238738 A1 | 9/2009 | Hurwitz et al. |

FOREIGN PATENT DOCUMENTS

| | | |
|---|---|---|
| WO | WO2010131253 A2 | 11/2010 |

OTHER PUBLICATIONS

PCT International Search Report for PCT/US2012/064442, dated Jan. 25, 2013.

*Primary Examiner* — Sean E Conley
(74) *Attorney, Agent, or Firm* — Honigman Miller Schwartz and Cohn LLP

(57) ABSTRACT

An apparatus for sanitizing a stethoscope head. The apparatus includes a housing, a reservoir disposed within the housing for containing the sanitizing fluid, one or more applicator pads mounted on the housing, and a dispensing valve for dispensing the sanitizing fluid from the reservoir onto the applicator pad.

18 Claims, 5 Drawing Sheets

APPARATUS AND METHOD FOR SANITIZING STETHOSCOPE HEADS

CROSS REFERENCE TO RELATED APPLICATIONS

This application is a 35 U.S.C. §371 United States National Phase Application of, and claims priority to, PCT International Application No. PCT/US2012/064442 filed Nov. 9, 2012, which claims the benefit under 35 U.S.C. §119 of U.S. Provisional Application Ser. No. 61/557,619 filed on Nov. 9, 2011. The entire contents of both of the aforesaid applications are incorporated by reference herein in their entireties.

BACKGROUND

Hospital-acquired infections are an issue in today's healthcare system. Such infections can lengthen hospital stays and increase health care costs. Hospital-acquired infections have many causes, including the transmission pathogenic microorganisms by contaminated medical devices. For this reason, the American Medical Association has passed a resolution recommending that stethoscopes (and other hand-held medical instruments) be cleaned between uses. See American Medical Association House of Delegates. *Proceedings of the 50th Interim Meeting*. Chicago, Ill.: American Medical Association; Dec. 8-11, 1996: 398. A need remains for a fast, easy, and cost-effective way to clean and disinfect stethoscope heads between patient uses.

SUMMARY

Accordingly, by utilizing the various embodiments described herein, medical practitioners are able to quickly, easily, and cost-effectively sanitize stethoscope heads between patient encounters at the point of care.

In one aspect, an apparatus is provided for dispensing a sanitizing fluid onto a stethoscope head. The apparatus includes a housing and a reservoir disposed within the housing for containing the sanitizing fluid. One or more applicator pads are mounted on the housing for applying the sanitizing fluid to the stethoscope head. A dispensing valve for dispensing the sanitizing fluid from the reservoir onto the applicator pads is also provided.

In another aspect, a method for sanitizing a stethoscope head comprises dispensing a sanitizing fluid from a reservoir onto an applicator pad, applying the sanitizing fluid to the stethoscope head by placing the stethoscope head in contact with the applicator pad, and sanitizing the stethoscope head with the sanitizing fluid.

Further objects, features, and advantages of the present invention will become apparent from consideration of the following descriptions and the appended claims when taken in connection with the accompanying drawings.

DETAILED DESCRIPTION

This disclosure is directed to an apparatus and method for sanitizing a stethoscope head. Utilizing the principles disclosed herein, medical practitioners are able to quickly, easily, and cost-effectively sanitize stethoscope heads between patient uses at the point of care.

Figure 1:
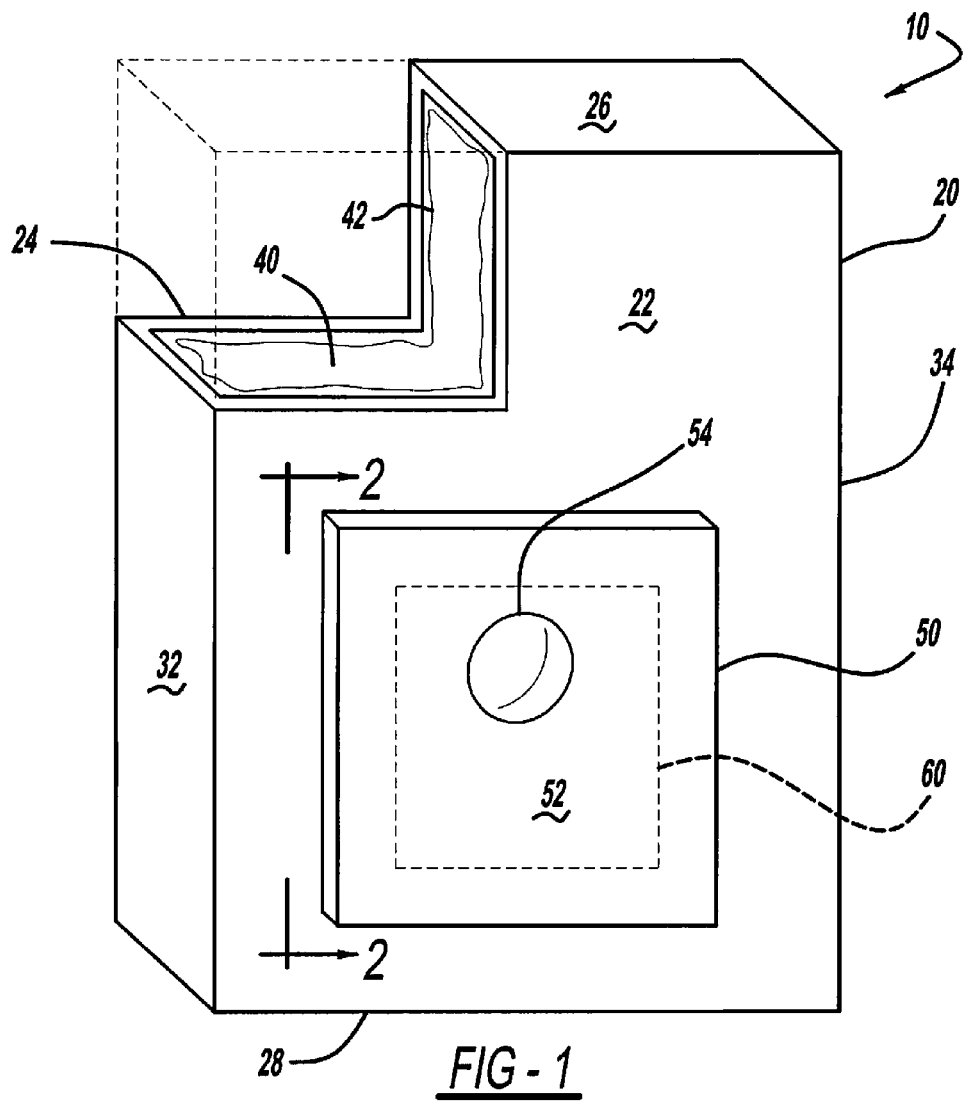
FIG. 1 is a front perspective/cut-away view of an apparatus for dispensing a sanitizing fluid onto a stethoscope head.

FIG. 1 illustrates a front perspective view of an apparatus 10 for dispensing a sanitizing fluid onto a stethoscope head. The apparatus 10 comprises, as its main components, a housing 20, a reservoir 40, one or more applicator pads 50, and a dispensing valve 60 for dispensing the sanitizing fluid from the reservoir 40 onto the one or more applicator pads 50.

The housing 20 is illustrated in FIG. 1 as having a rectangular shape. In this embodiment, the housing 20 has a front wall 22, a back wall 24, and side walls, including a top wall 26, a bottom wall 28, a left wall 32, and a right wall 34. However, as one having ordinary skill in the art will readily understand, the housing 20 may have any suitable shape.

The reservoir 40 is disposed within the housing 20 and is configured to contain the sanitizing fluid. In FIG. 1, the upper left corner of the housing 20 is cut away to reveal the reservoir 40 inside the housing 20. In some embodiments (not shown), the walls of the housing 20 itself define the reservoir 40. In these embodiments, the supply of sanitizing fluid may be replenished by pouring additional sanitizing fluid into the housing 40 through an aperture (not shown).

In other embodiments, the reservoir 40 is a separate container inside the housing 20. For example, as shown in FIG. 1, the reservoir 40 may be a bag 42 within which the sanitizing fluid is contained. In these embodiments, the supply of sanitizing fluid may be replenished by replacing an empty bag 42 with a new bag 42 full of sanitizing fluid.

The one or more applicator pads 50 are mounted on the housing 20 and are configured to apply the sanitizing fluid to the stethoscope head. In the apparatus 10 shown in FIG. 1, an applicator pad 50 is mounted on the front wall 22 of the housing 20. However, the applicator pad 50 may be mounted on any other wall or walls of the housing 20.

In some embodiments, the applicator pad 50 is constructed from a porous, absorbent material configured to absorb the sanitizing fluid. For example, the applicator pad may be constructed from a cloth material, a cellulose sponge material, a synthetic polymer sponge material, or any other suitably porous and absorbent material.

In some embodiments, the applicator pad 50 has a thickness sufficient to absorb an effective quantity of sanitizing fluid to sanitize a stethoscope head. The effective quantity of sanitizing fluid may differ depending on the particular sanitizing fluid used with a given apparatus 10.

Figure 2:
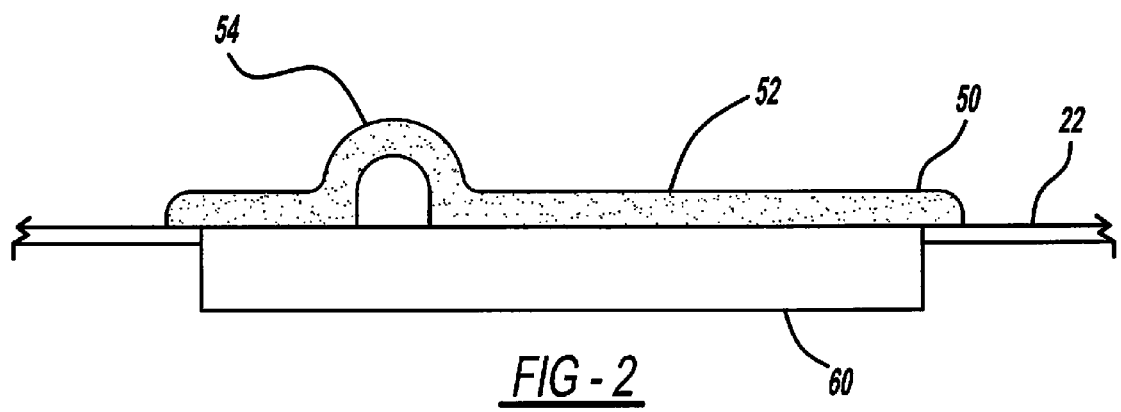
FIG. 2 is a cross-sectional view of a portion of the apparatus seen in FIG. 1.

In one embodiment, the applicator pad 50 is configured to facilitate the application of sanitizing fluid to the diaphragm D and/or the bell B of a stethoscope head S. Thus, the applicator pad 50 may have a substantially planar portion 52, shown in FIG. 2 and FIG. 7b, for applying the sanitizing fluid to the flat surface of the diaphragm D of the stethoscope head S. The applicator pad 50 also may have a dome-shaped portion 54 for applying the sanitizing fluid to the inside of the bell B of the stethoscope head S. The dome-shaped portion 54 is configured in a rounded shape suitable to extend into the bell B of a stethoscope head S. For example, as shown in FIG. 2 and FIG. 7c, the dome-shaped portion 54 may have a substantially hemi-spherical shape, with a radius between about 0.50 and about 1.00 cm, permitting the dome-shaped portion 54 to extend into the bell B. In other embodiments, the applicator pad 50 is configured to accommodate alternately shaped stethoscope heads or other devices.

As shown in FIGS. 1 and 2, the substantially flat portion 52 and the dome-shaped portion 54 of the applicator pad 50 may be disposed adjacently to one another on the housing and may be formed from a single piece of porous, absorbent material, defining a single applicator pad 50. In other embodiments, the substantially flat portion 52 and the dome-shaped portion 54 may be formed from separate pieces of porous, absorbent material, defining more than one applicator pad 50, and/or may be disposed on non-adjacent portions of the housing 20.

Referring again to FIGS. 1 and 2, the apparatus 10 also includes a dispensing valve 60 for dispensing the sanitizing fluid from the reservoir 40 onto the applicator pad 50. In one embodiment, the dispensing valve 60 has a dispensing state and a non-dispensing state, and is configured to dispense the sanitizing fluid from the reservoir 40 onto the applicator pad 50 only when the dispensing valve 60 is in the dispensing state. Particularly, the dispensing valve 60 is configured to dispense the sanitizing fluid from the reservoir 40 onto the applicator pad 50 when pressure is applied to the applicator pad 50. For example, the dispensing valve 60 may be configured to deliver an aliquot of sanitizing fluid to the applicator pad 50 when a stethoscope head is placed or pushed in contact with the applicator pad 50. In one embodiment, the dispensing valve 60 is configured to deliver a sufficiently large aliquot of sanitizing fluid to saturate the applicator pad 50 with the sanitizing fluid.

As shown in FIGS. 1 and 2, where the applicator pad 50 includes a substantially planar portion 52 and a dome-shaped portion 54, the dispensing valve 60 may be configured to dispense the sanitizing fluid independently onto the substantially planar and dome-shaped portions 52 and 54 of the one or more applicator pads 50. In other words, the dispensing valve 60 may be configured to dispense the sanitizing fluid onto the substantially planar portion 52 without dispensing sanitizing fluid onto the dome-shaped portion 54, and vice versa. For example, if the diaphragm of a stethoscope head is placed in contact with the substantially planar portion 52 of the applicator pad 50, the dispensing valve 60 may dispense the sanitizing fluid onto the substantially planar portion 52, but not onto the dome-shaped portion 54.

In FIG. 2, the dispensing valve for dispensing the sanitizing fluid from the reservoir 40 onto the applicator pad 50 is shown schematically as box 60. Thus, it will be understood that the dispensing valve 60 may be any suitable valve known in the art for controllably delivering aliquots of a fluid. For example, the dispensing valve 60 may be a mechanical pump, such as a pump that discharges the sanitizing fluid upon the depression of a plunger, or an electric pump powered by direct or alternating current. The dispensing valve 60 may also be a plurality of orifices or valves in a deflectable wall portion of the housing. In one embodiment, the dispensing valve 60 is configured to dispense sanitizing fluid onto the applicator pad 50 when pressure is applied to the applicator pad 50. However, the dispensing valve 60 may also be configured to dispense the sanitizing fluid onto the applicator pad 50 in response to mechanical or electrical signals received from a remote input device, e.g., a lever or button (not shown) provided elsewhere on the housing.

Figure 3A:
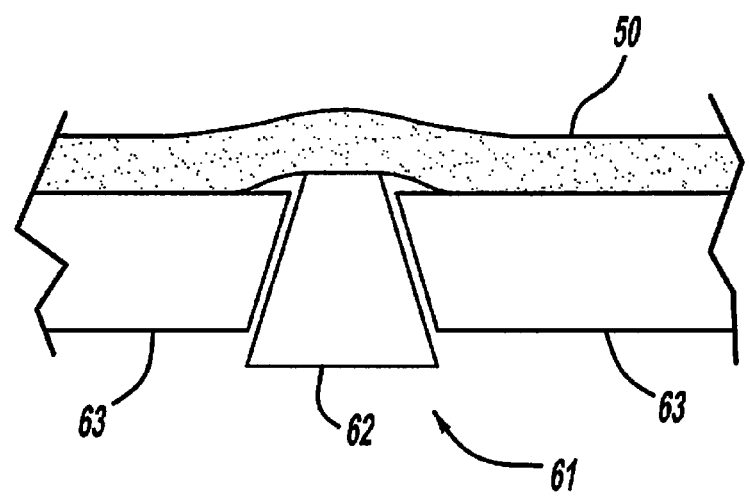
FIGS. 3a and 3b are cross-sectional views of a depressible plunger valve for dispensing sanitizing fluid.
Figure 3B:
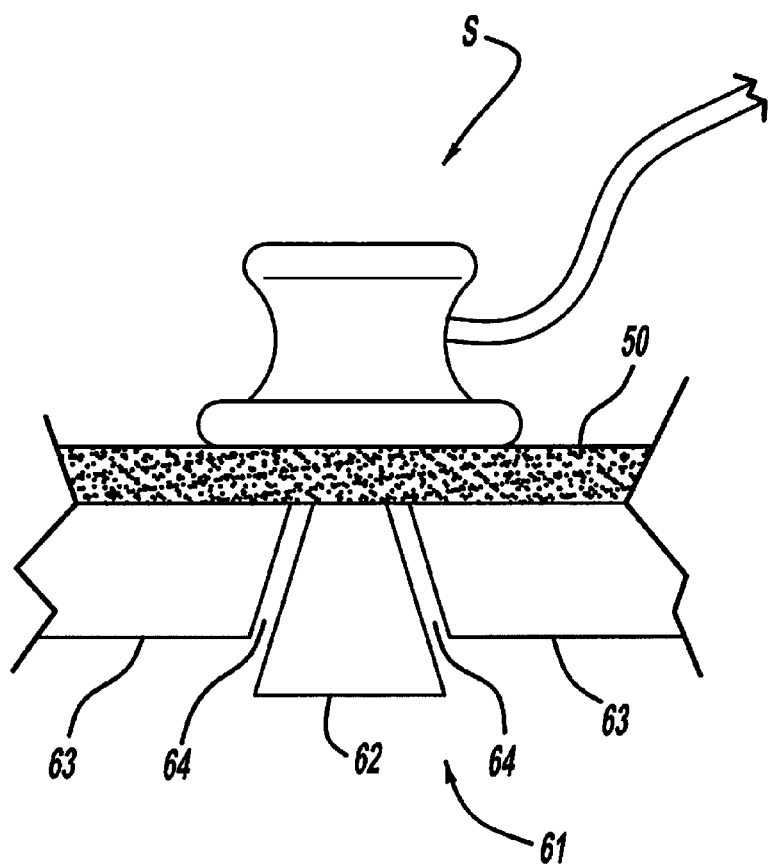

In one exemplary embodiment, shown in FIGS. 3a and 3b, the dispensing valve for dispensing sanitizing fluid is a depressible plunger valve 61 disposed behind the applicator pad 50. The depressible plunger valve 61 comprises a plunger portion 62 and a wall portion 63. The wall portion 63 may be unitarily formed with or attached to one of the walls of the housing 20 (e.g., the front wall 22). In the non-dispensing state, shown in FIG. 3a, the plunger portion 62 fills an orifice in the wall portion 63, preventing sanitizing fluid from flowing through the orifice onto the applicator pad 50. As shown in FIG. 3b, when pressure is applied to the applicator pad 50, such as by placing a stethoscope head S in contact with the applicator pad 50, the plunger portion 62 is depressed, providing passages 64 for the sanitizing fluid to flow from the reservoir to the applicator pad 50 (i.e., the dispensing state). The darkened shading of the applicator pad 50 in FIG. 3b indicates that the applicator pad 50 has been wetted with the sanitizing fluid. The plunger portion 62 may be spring-loaded to remain in the orifice, such that the plunger valve 61 is biased toward the non-dispensing state.

Figure 4A:
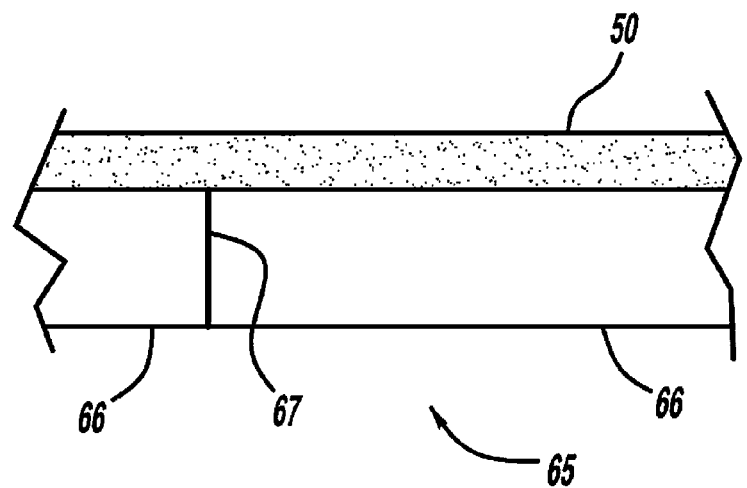
FIGS. 4a and 4b are cross-sectional views of a slit valve for dispensing sanitizing fluid.
Figure 4B:
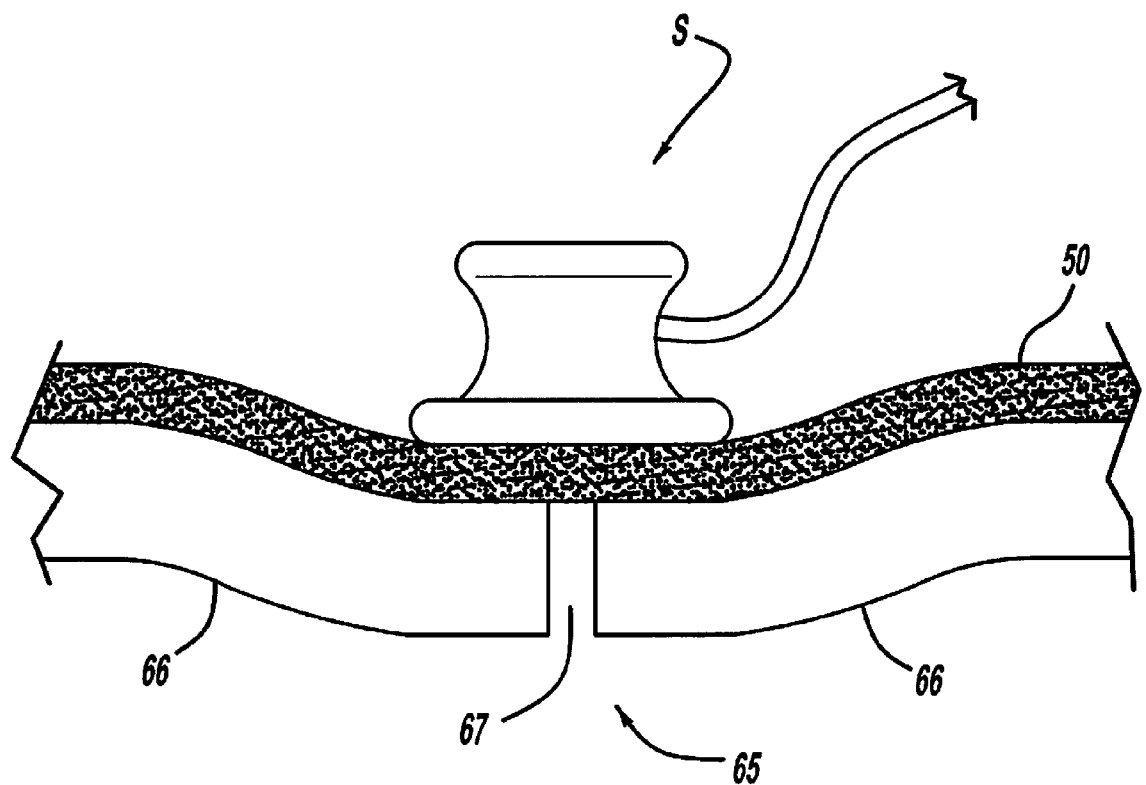

In another exemplary embodiment, shown in FIGS. 4a and 4b, the dispensing valve for dispensing sanitizing fluid is a slit valve 65. The slit valve 65 comprises a deflectable wall portion 66 and a slit 67. The deflectable wall 66 may be unitarily formed with or attached to one of the walls of the housing 20 (e.g., the front wall 22). In the non-dispensing state, shown in FIG. 4a, the deflectable wall 66 lies substantially in a plane, and the slit 67 is closed, preventing sanitizing fluid from flowing onto the applicator pad 50. As shown in FIG. 4b, when pressure is applied to the applicator pad 50, such as by placing a stethoscope head S in contact with the applicator pad 50, the deflectable wall 66 is deflected out of the plane, causing the slit 67 to open and allowing sanitizing fluid to flow from the reservoir to the applicator pad 50 (i.e., the dispensing state). The darkened shading of the applicator pad 50 in FIG. 4b indicates that the applicator pad 50 has been wetted with the sanitizing fluid.

Figures 5A, 5B:
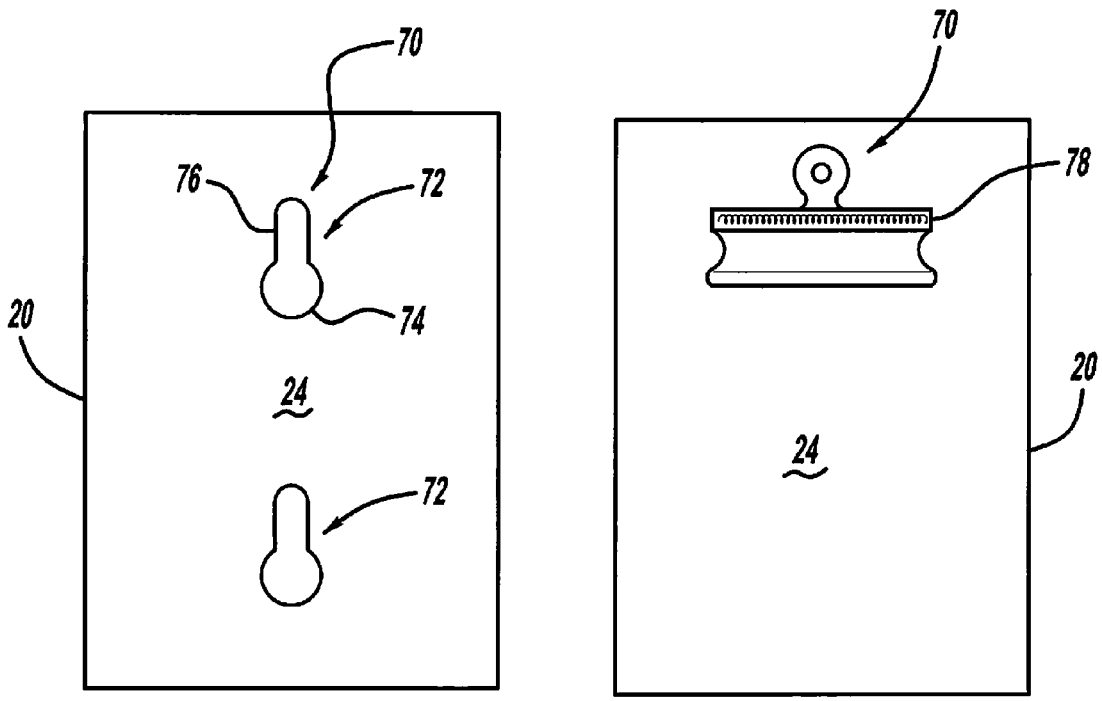
FIGS. 5a and 5b are alternate rear views illustrating various mounts for the apparatus seen in FIG. 1.

Referring now to FIGS. 5a and 5b, the apparatus 10 may further comprise a mount 70 for mounting the apparatus 10 on a variety of supporting structures, such as a wall or piece of furniture. In one embodiment, the mount 70 is configured for wall-mounting of the apparatus 10 and disposed on the back wall 24 of the housing 20. One particular construction employs one or more slots 72 in the back wall 24 of the housing 20. The slots 72 may be configured for mounting the apparatus 10 on one or more nail or screw heads, such as for mounting the apparatus 10 on a wall. As such, the slots 72 may be key-hole slots and have a rounded lower portion 74 for accepting the nail or screw head through the slot 72 and a narrow upper portion 76 for sliding over the shaft of the nail or screw positioned therein.

In another embodiment, shown in FIG. 5b, the mount 70 may be a spring-loaded clip 78 attached to the back wall 24 of the housing 20. The clip 78 permits the apparatus 10 to be removably mounted on an object of furniture, such as a bed frame, at the point of care. The clip 78 may also be used to mount the apparatus 10 on a medical practitioner's clipboard or allow it to double as a clipboard.

Figure 6:
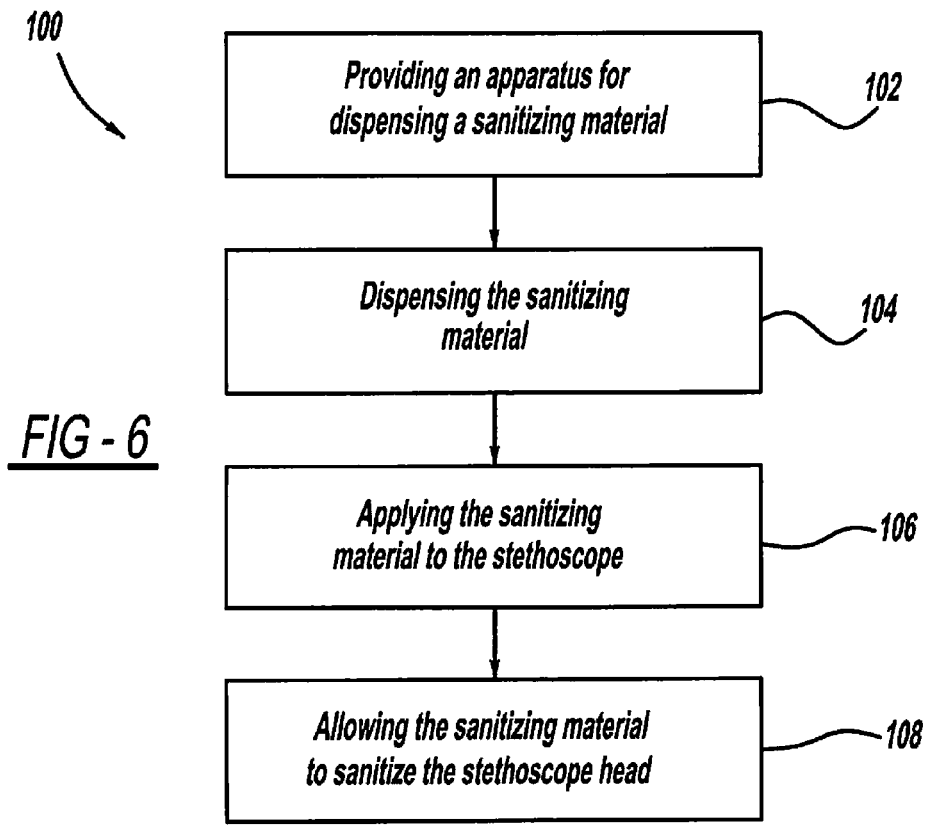
FIG. 6 is a flowchart depicting a method for sanitizing a stethoscope head.

Referring now to FIG. 6, a method 100 for sanitizing a stethoscope head is provided. As indicated in box 102, the method 100 comprises providing an apparatus 10 for dispensing a sanitizing fluid. The apparatus 10 may be constructed in accordance with the presently disclosed apparatus, as described above. Thus, the apparatus 10 may comprise a housing 20, a reservoir 40 disposed within the housing 20 and containing the sanitizing fluid, one or more applicator pads 50 mounted on the housing 10, and a dispensing valve 60 for dispensing the sanitizing fluid from the reservoir 40 onto the one or more applicator pads 50.

The sanitizing fluid contained in the reservoir 40 of the apparatus 10 may be any fluid known in the art to be suitable for disinfecting surfaces. For example, the sanitizing fluid may be an alcohol-based disinfectant, a benzalkonium chloride-based disinfectant, or any other fluid suitable for disinfecting surfaces. A benzalkonium chloride-based disinfectant, known as the surfactant, allantoin, and benzalkonium chloride ("SAB") disinfectant has been described previously. See, e.g., David L. Dyer et al., *Testing a New Alcohol-Free Hand Sanitizer to Combat Infection*, 68 AORN J. 239 (1998), the entire contents of which are incorporated herein by reference. In one embodiment, the sanitizing fluid is an alcohol-based disinfectant, such as an ethanol- or isopropanol-based disinfectant, or any other suitable alcohol-based disinfectant.

Figure 7A:
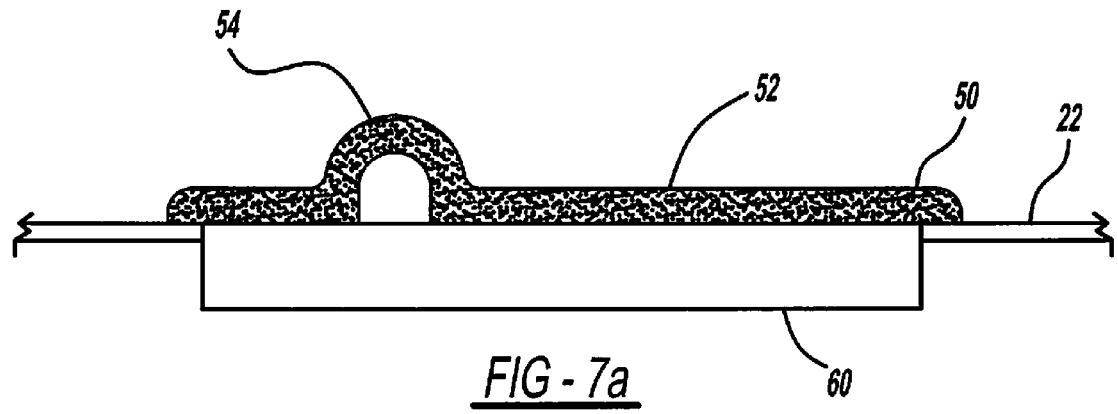
FIGS. 7a-7c are cross-sectional views, similar to FIG. 2, showing a stethoscope being sanitized.

As indicated in box 104, and as illustrated in FIG. 7*a*, during use of the apparatus 10, sanitizing fluid is dispensed from the reservoir onto the applicator pad 50. The darkened shading of the applicator pad 50 in FIG. 7*a* indicates that the applicator pad 50 is saturated with sanitizing fluid. In some embodiments, where the dispensing valve 60 is pressure-activated, the sanitizing fluid is dispensed onto the applicator pad 50 when a medical practitioner applies pressure to the applicator pad 50 with a stethoscope head.

Figure 7B:
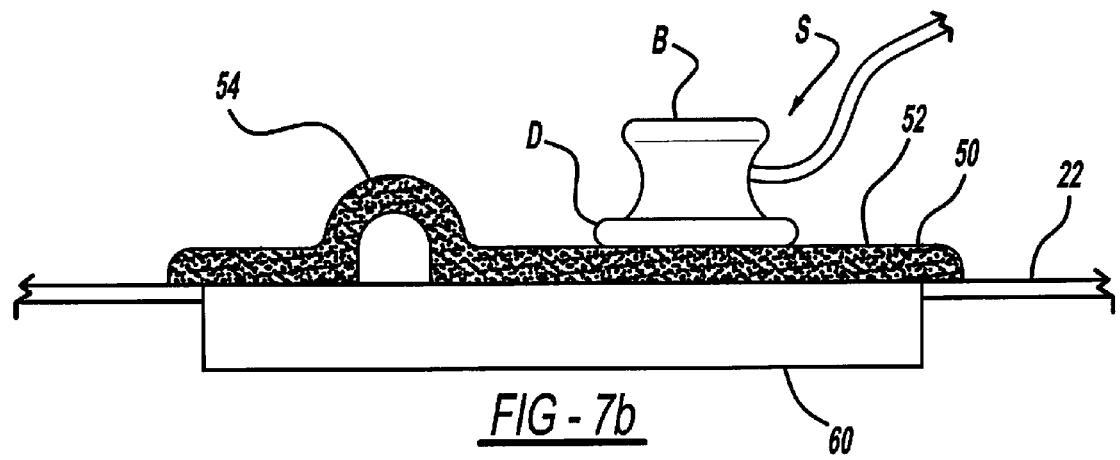
Figure 7C:
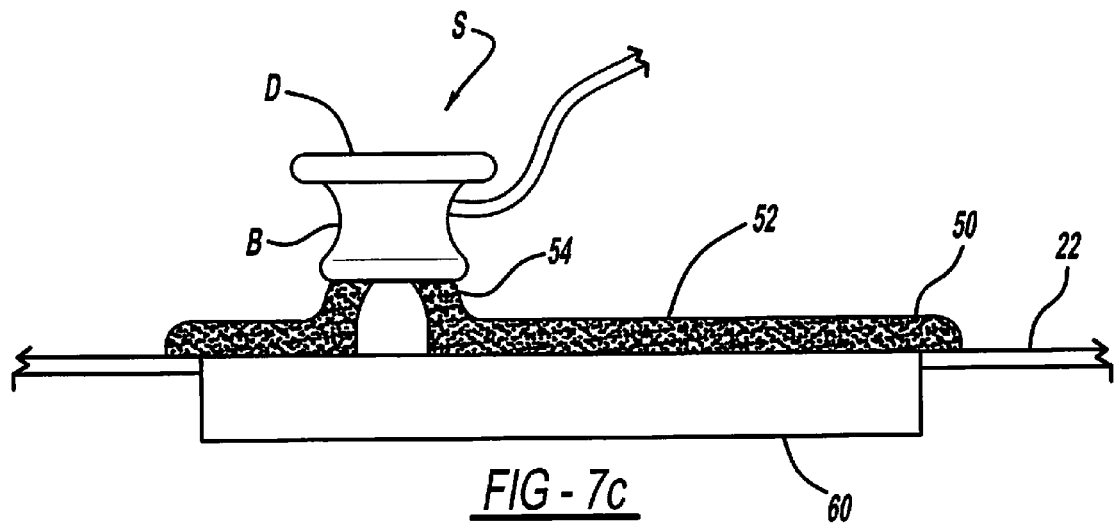

As indicated in box 106, and as illustrated in FIGS. 7*b* and 7*c*, a practitioner applies the sanitizing fluid to the stethoscope head S by placing the stethoscope head S in contact with the applicator pad 50. When the stethoscope head S is placed in contact with the applicator pad 50, the sanitizing fluid is transferred from the applicator pad 50 to the stethoscope head S. In some cases, it may be necessary to draw the stethoscope head S across the applicator pad 50 or to compress the applicator pad 50 with the stethoscope head S to squeeze the sanitizing fluid out of the applicator pad 50 and onto the stethoscope head S. Where the dispensing valve 60 is pressure-activated, the pressure of the stethoscope head S against the applicator pad 50 activates the dispensing valve 60 to dispense additional sanitizing fluid from the reservoir 40 onto the applicator pad 50.

In some embodiments, as shown in FIGS. 7*b* and 7*c* and mentioned above, the applicator pad 50 has a substantially planar portion 52 for applying the sanitizing fluid to the diaphragm D of the stethoscope head S and has a dome-shaped portion 54 for applying the sanitizing fluid to the inside of the bell B of the stethoscope head S. In these embodiments, the sanitizing fluid is applied to the diaphragm D by placing the diaphragm D in contact with the substantially planar portion 52, and the sanitizing fluid is applied to the bell B by placing the bell B in contact with the dome-shaped portion 54 (i.e., by placing the bell B over the dome-shaped portion 54, such that the dome-shaped portion 54 extends into the bell B).

As indicated in box 108, after contacting the stethoscope S with the sanitizing fluid, the practitioner allows the sanitizing fluid to remain in contact with the diaphragm D or bell B for a time sufficient to sanitize the stethoscope head. Where the sanitizing fluid is an alcohol-based disinfectant, the sanitizing fluid sanitizes the stethoscope head as it evaporates. In one embodiment, in order to avoid contaminating the sanitized stethoscope head, the medical practitioner does not warm the stethoscope on their hand after sanitization.

While the present apparatus and method have been described in terms of certain particular embodiments, it will be understood that the apparatus and method are not limited to the disclosed embodiments, as those having skill in the art may make various modifications without departing from the scope of the following claims.

We claim:

1. An apparatus for dispensing a sanitizing fluid onto a stethoscope head, the apparatus comprising:

a housing;

a reservoir disposed within the housing and configured to contain a sanitizing fluid;

an applicator pad mounted on the housing for applying the sanitizing fluid to the stethoscope head, the applicator pad comprising a dome-shaped portion having a substantially hemi-spherical shape configured to extend into an interior region of a bell of the stethoscope head when the bell portion is placed over the dome-shaped portion; and a dispensing valve for dispensing the sanitizing fluid from the reservoir onto the applicator pad, the applicator pad comprising the dome-shaped portion is formed from an absorbent material configured to absorb the sanitizing fluid when the dispending valve dispenses the sanitizing fluid from the reservoir onto the applicator pad;

wherein the dispensing valve for dispensing is configured to dispense the sanitizing fluid from the reservoir onto the applicator pad when the pressure is applied to the applicator pad; and wherein the dispensing valve for dispending is a slit valve disposed behind the applicator pad.

2. The apparatus of claim 1, wherein the dispensing valve for dispensing has a dispensing state and a non-dispensing state, the dispensing valve for dispensing being configured to dispense the sanitizing fluid from the reservoir onto the applicator pad only when the dispensing valve for dispensing is in the dispensing state.

3. An apparatus, for dispensing a sanitizing fluid onto a stethoscope head, the apparatus comprising:

a housing;

a reservoir disposed within the housing and configured to contain a sanitizing fluid;

an applicator pad mounted on the housing for applying the sanitizing fluid to the stethoscope head, the applicator pad comprising a dome-shaped portion having a substantially hemi-spherical shape configured to extend into an interior region of a bell of the stethoscope head when the bell is placed over the dome-shaped portion; and a dispensing valve for dispensing the sanitizing fluid from the reservoir onto the applicator pad, the applicator pad comprising the dome-shaped portion is formed form a porous, absorbent material configured to absorb the sanitizing fluid when the dispensing valve dispenses the sanitizing fluid from the reservoir onto the applicator pad;

wherein the dispensing valve for dispensing is configured to dispense the sanitizing fluid from the reservoir onto the applicator pad when pressure is applied to the applicator pad; and wherein the dispensing valve for dispensing is a depressible plunger valve disposed behind the applicator pad.

4. The apparatus of claim 3, wherein the porous, absorbent material of the applicator pad comprises one of a cloth material, a cellulose sponge material, or a synthetic polymer sponge material.

5. The apparatus of claim 3, wherein the applicator pad further comprises a substantially planar portion configured to receive a diaphragm of the stethoscope head when the surface of the diaphragm is placed in contact with the substantially planar portion of the applicator pad.

6. The apparatus of claim 5, wherein the substantially hemi-spherical shape of the dome-shaped portion has a radius between about 0.50 and 1.00 cm.

7. The apparatus of claim 5, wherein the dispensing valve for dispensing is configured to dispense the sanitizing fluid independently onto the substantially planar and dome-shaped portions of the applicator pad.

8. The apparatus of claim 5, wherein the substantially planar portion is formed from the porous, absorbent material configured to absorb the sanitizing fluid when the dispensing valve dispenses the sanitizing fluid from the reservoir onto the applicator pad.

9. The apparatus of claim 3, wherein the porous, absorbent material of the dome-shaped portion comprises a sponge material.

10. The apparatus of claim 3, wherein the housing has a back wall and a front wall, the applicator pad being mounted on the front wall of the housing, the apparatus further comprising a mount disposed on the back wall of the housing.

11. The apparatus of claim 10, wherein the mount is configured for wall-mounting.

12. The apparatus of claim 11, wherein the mount comprises one or more slots in the back wall of the housing, the slots being configured for mounting on a nail- or screw-head.

13. The apparatus of claim 10, wherein the mount comprises a spring-loaded clip attached to the back wall of the housing.

14. A method for sanitizing a stethoscope head having a diaphragm and a bell, the method comprising the steps of:
providing an apparatus for dispensing a sanitizing fluid, the apparatus comprising:
a housing;
a reservoir disposed within the housing and containing the sanitizing fluid;
an applicator pad mounted on the housing, the applicator pad comprising a dome-shaped portion having a substantially hemi-spherical shape configured to extend into an interior region of the bell when the bell is placed over the dome-shaped portion; and
a dispensing valve for dispensing the sanitizing fluid from the reservoir onto the applicator pad, wherein the dispensing valve for dispensing is configured to dispense the sanitizing fluid from the reservoir onto the applicator pad when pressure is applied to the applicator pad, and wherein the dispensing valve for dispensing is a slit valve disposed behind the applicator pad;
dispensing the sanitizing fluid from the reservoir onto the applicator pad, the applicator pad comprising the dome-shaped portion is formed from a porous, absorbent material that absorbs the sanitizing fluid when the dispensing valve dispenses the sanitizing fluid from the reservoir onto the applicator pad;
applying the sanitizing fluid to the bell of the stethoscope head by placing the bell over the dome-shaped portion; and
allowing the sanitizing fluid to sanitize the bell of the stethoscope head.

15. The method of claim 14, wherein the sanitizing fluid is an alcohol-based disinfectant or an SAB disinfectant.

16. The method of claim 14, wherein the applicator pad further comprises a substantially planar portion for applying the sanitizing fluid to the diaphragm; and wherein the step of applying the sanitizing fluid to the bell of the stethoscope head further comprises:
applying the sanitizing fluid to the diaphragm by placing the diaphragm in contact with the substantially planar portion.

17. The method of claim 14, wherein the step of dispensing the sanitizing fluid comprises applying pressure to the applicator pad with the stethoscope head.

18. A method for sanitizing a stethoscope head having a diaphragm and a bell, the method comprising the steps of:
providing an apparatus for dispensing a sanitizing fluid, the apparatus comprising:
a housing;
a reservoir disposed within the housing and containing the sanitizing fluid;
an applicator pad mounted on the housing, the applicator pad comprising a dome-shaped portion having a substantially hemi-spherical shape configured to extend into an interior region of the bell when the bell is placed over the dome-shaped portion; and
a dispensing valve for dispensing the sanitizing fluid from the reservoir onto the applicator pad, wherein the dispensing valve for dispensing is configured to dispense the sanitizing fluid from the reservoir onto the applicator pad when pressure is applied to the applicator pad, and wherein the dispensing valve for dispensing is a depressible plunger valve disposed behind the applicator pad;
dispensing the sanitizing fluid from the reservoir onto the applicator pad, the applicator pad comprising the dome-shaped portion is formed from a porous, absorbent material that absorbs the sanitizing fluid when the dispensing valve dispenses the sanitizing fluid from the reservoir onto the applicator pad;
applying the sanitizing fluid to the bell of the stethoscope head by placing the bell over the dome-shaped portion; and
allowing the sanitizing fluid to sanitize the bell of the stethoscope head.

* * * * *

UNITED STATES PATENT AND TRADEMARK OFFICE
CERTIFICATE OF CORRECTION

PATENT NO. : 9,138,500 B2
APPLICATION NO. : 14/357523
DATED : September 22, 2015
INVENTOR(S) : Mark D. Kolins et al.

It is certified that error appears in the above-identified patent and that said Letters Patent is hereby corrected as shown below:

On the title page of the patent:

(71) Applicant: Please delete "William Beaumont Hospital, Royal Oak, MI (US)" and insert --Mark D. Kolins, Bloomfield Hills, MI (US) and Barry Siegel, Birmingham, MI (US)--.

(72) Inventor: Please correct Mark D. Kolins' address to "Bloomfield Hills, MI (US)".

Signed and Sealed this
First Day of December, 2015

Michelle K. Lee
*Director of the United States Patent and Trademark Office*